| United States Patent [19]
Ellard et al.

[11] 4,306,064
[45] Dec. 15, 1981

[54] SYNTHESIS OF 2,4-DIAMINO-6-HYDROXYMETHYLPTERIDINE

[76] Inventors: James A. Ellard; Joseph Satanek, Jr., both of 1515 Nicholas Rd., Dayton, Ohio 45407

[21] Appl. No.: 133,788

[22] Filed: Mar. 25, 1980

[51] Int. Cl.³ .......................................... C07D 475/08
[52] U.S. Cl. .................................................. 544/260
[58] Field of Search ........................................ 544/260

[56] References Cited

U.S. PATENT DOCUMENTS 3,989,703  11/1976  Niculescu-Duvaz et al. ...... 544/260
4,080,325   3/1978  Ellard ................................. 544/260

OTHER PUBLICATIONS

Boyle et al., Chem. Ber., 113, 1514–1523, No. 4, Apr. 1980.

Primary Examiner—Paul M. Coughlan, Jr.
Attorney, Agent, or Firm—John S. Roberts, Jr.

[57] ABSTRACT

In a method of preparing methotrexate from a coupling of 2,4-bis(triphenylphosphazino)-6-bromomethylpteridine hydrobromide with ethyl N-(p-methylamino)-benzoyl-L-glutamate to produce the phosphazino derivative of methotrexate ester and subsequently hydrolyzing the phosphazino and ester groups to produce the free methotrexate, the pteridine synthesis step wherein molecular oxygen is substituted for reaction air and the pH throughout the pteridine synthesis is regulated to between 2.5 and 5.4, the preferred pH being about 3.0 and producing from tetraaminopyrimidine and dihydroxyacetone the isomer 2,4-diamino-6-hydroxymethylpteridine over 2,4-diamino-7-hydroxymethylpteridine in a ratio of about 20:1. Exemplary of other situations involving pteridine where the molecular oxygen may be substituted for reaction air are: in the production of folic acid, tetrahydrofolic acid, etc.

1 Claim, No Drawings

SYNTHESIS OF 2,4-DIAMINO-6-HYDROXYMETHYLPTERIDINE

The invention described herein was made in the course of work under a contract from the Department of Health, Education, and Welfare.

The invention disclosed herein is, in a method of preparing methotrexate from a coupling of 2,4-bis(triphenylphosphazino)-6-bromomethylpteridine hydrobromide with ethyl N-(p-methylamino) benozyl-L-glutamate to produce the phosphazino derivative of methotrexate ester and subsequently hydrolyzing the phosphazino and ester groups to produce the free methotrexate, the pteridine synthesis step wherein molecular oxygen is substituted for reaction air and the pH throughout the coupling is regulated to between 2.5 and 5.4, the preferred pH being about 3.0 and producing from tetraaminopyrimidine and dihydroxyacetone the isomer 2,4-diamino-6-hydroxymethylpteridine over 2,4-diamino-7-hydroxymethylpteridine in a ratio of about 20:1.

PRIOR ART STATEMENT

C. M. Baugh and E. Shaw, *J. Org. Chem.*, 29:3610 (1964).

J. R. Piper and J. A. Montgomery, *J. Het. Chem.*, 11:279 (1974).

J. R. Piper and J. A. Montgomery, *J. Org. Chem.*, 42:208 (1977).

U.S. Pat. No. 4,080,325 Ellard.

The patent of Ellard, U.S. Pat. No. 4,080,325, is believed uniquely to be the closest art. Of interest is that the struggle for the production of methotrexate has been assisted by the U.S. Government in the effort to bring this compound in sufficient amount to clinical trial. Relative to the present application, the pertinent passages in U.S. Pat. No. 4,080,325 appear to be column 1, lines 55–68, as well as the equation noted at column 2. The optimum pH was 5.5 to give the desired 6-hydroxymethylpteridine isomer used in the reaction. The relationship of the unwanted isomers is shown in the equation at column 2, lines 40–50. It was found that the reaction time from the parameters given in the patent might be reduced to 3–6 hours and yields increased to 60–75% of the desired isomer 2,4-diamino-6-hydroxymethylpteridine. Reaction pH is lowered from about 5.4 to 3.5 or optimally 3.0. The reaction is complete in 3–6 hours and the yield is 60–65% with an isomer ratio (2,4-diamino-6-hydroxymethylpteridine/2,4-diamino-7-hydroxymethylpteridine) of approximately 20:1. Comparison aeration with air instead of oxygen at a comparable pH, say 3.5, has been shown to yield an abundance of 2,4-diamino-6-methylpteridine rather than the desired 2,4-diamino-6-hydroxymethylpteridine.

EXAMPLE 1

This example consists of improvements in a process previously designated as the multi-step Piper-Montgomery process for the production of antifolate methotrexate and previously described in U.S. Pat. No. 4,080,325.

The Piper-Montgomery process commenced with 2,4,5,6-tetraaminopyrimidine sulfite as one starting material and is usually produced in the form of the bisulfite in an acetate buffer. The present modification positively produced the hydrochloride from the bisulfite and eliminated the acetate buffer utilized in other processes. Subsequently, a pteridine ring was formed from the pyrimidine hydrochloride using dihydroxyacetone at pH now of 2.5 to 5.4 to form the second ring. It is of great importance in this present invention that pure oxygen be utilized or molecular oxygen be utilized as a reagent. The low acid pH control, together with the use of hydrochloride salts minus the acetate buffer, assisted in preferentially favoring the formation of 2,4-diamino-6-hydroxymethylpteridine to the extent of about a ratio of 20:1 over the 7-hydroxymethyl isomer variety. Subsequently, the 6-hydroxymethyl compound is converted to the hydrobromide acid salt and reacted with three moles of a triphenyldibromophosphorane and phosphazine protecting groups were formed on the amine groups of the pteridine ring as the 6-hydroxymethyl group was transformed to B 6-bromomethyl, a key intermediate.

The present process left the protecting phosphazine groups on the primary amine groups to discourage side reaction during subsequent alkylation of the major reactant ethyl-N-(p-methylaminobenzoyl)-L-glutamate. The high methotrexate yields arose in part from the MgO change in the coupling process.

EXAMPLE 2

In the manner of Example 1, a series of runs was made utilizing oxygen (molecular oxygen) rather than air. It was found that the use of oxygen decreased the amount of by-product methylpteridine formed. Twin results also occurred in that the use of oxygen greatly increased the reaction rate of the desired sequence of reactions, but, on the other hand, the formation of the isomeric product was actually increased. Thus, the statement was made of this sequence of reactions that the more rapid reaction was less selective. As a correlating parameter, the use of lower pH values was, in the words of the researcher, delightful in that the formation of the desired product was more rapid as well as more selective.

At pH values of 3.0–3.5, the reaction was completed in 2–4 hours and the product was about 95% desired product with 5% or less of the isomeric 2,4-diamino-7-hydroxymethylpteridine and a very slight amount of methyl pteridine. Purification for subsequent synthesis was thus through this example greatly simplified.

We claim:

1. In a method of producing 2,4-diamino-6-hydroxymethylpteridine from tetraaminopyrimidine and dihydroxyacetone, the step of favorably producing the isomer 2,4-diamino-6-hydroxymethylpteridine over the unwanted 2,4-diawherein the pH is kept at about 3.0 and oxygen is used instead of air as an oxidant and as a reaction atmosphere.

* * * * *